(12) United States Patent
Tsurizumi et al.

(10) Patent No.: US 8,616,217 B2
(45) Date of Patent: Dec. 31, 2013

(54) SMOKING ARTICLE

(71) Applicant: Japan Tobacco Inc., Tokyo (JP)

(72) Inventors: Ryutaro Tsurizumi, Tokyo (JP); Hiroshi Sasaki, Tokyo (JP); Naoki Hamamoto, Tokyo (JP); Tomoichi Watanabe, Tokyo (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 13/626,444

(22) Filed: Sep. 25, 2012

(65) Prior Publication Data

US 2013/0019888 A1 Jan. 24, 2013

Related U.S. Application Data

(63) Continuation of application No. PCT/JP2010/055365, filed on Mar. 26, 2010.

(51) Int. Cl.
*A24F 1/32* (2006.01)

(52) U.S. Cl.
USPC .......................................... 131/194; 131/361

(58) Field of Classification Search
USPC ................................................ 131/194, 361
See application file for complete search history.

(56) References Cited

U.S. PATENT DOCUMENTS

| | | | |
|---|---|---|---|
| 4,732,168 A * | 3/1988 | Resce et al. ................... | 131/359 |
| 4,854,331 A * | 8/1989 | Banerjee et al. .............. | 131/194 |
| 4,991,606 A | 2/1991 | Serrano et al. | |
| 5,020,548 A | 6/1991 | Farrier et al. | |
| 2009/0044818 A1 | 2/2009 | Takeuchi et al. | |

FOREIGN PATENT DOCUMENTS

| | | |
|---|---|---|
| JP | 63-54357 B2 | 10/1988 |
| JP | 6-75598 B2 | 9/1994 |
| JP | 3012253 B2 | 12/1999 |
| WO | WO 2007/119678 A1 | 10/2007 |

* cited by examiner

*Primary Examiner* — Richard Crispino
*Assistant Examiner* — Dionne Walls Mayes
(74) *Attorney, Agent, or Firm* — Birch, Stewart, Kolasch & Birch, LLP

(57) ABSTRACT

A smoking article comprises a multilayered tube member (9) including at least one metal layer and one paper layer, a carbon heat source (4) arranged in an end portion of the tube member (9) to be at least partly in direct close contact with an inner surface of the tube member (9), the carbon heat source emitting heat when ignited, a smoking flavor releasing source (8) arranged in the tube member (9) to adjoin the carbon heat source (4), and a holder part (14) keeping the carbon heat source (4) in direct contact with said end portion and holding the carbon heat source (4) against said end portion.

6 Claims, 4 Drawing Sheets

SMOKING ARTICLE

CROSS REFERENCE TO RELATED APPLICATION

This application is a continuation of PCT/JP2010/055365 filed on Mar. 26, 2010,which is hereby expressly incorporated by reference into the present application.

This invention relates to a smoking article having a carbon heat source.

BACKGROUND ART

Smoking articles with a carbon heat source arranged at an end to transfer heat to a smoking flavor releasing source are known (see patent document 1, for example). In the smoking article disclosed in patent document 1, the carbon heat source is enclosed in a heat-insulating jacket formed from a glass mat or the like and held at an end of the smoking article by elasticity of the heat-insulating jacket. This way of holding the heat source is costly because of use of the heat-insulating jacket formed from a glass mat or the like. It also takes a step of wrapping the heat source in a glass mat. There is also concern that the carbon heat source enclosed in the heat-insulating jacket may exhibit problems such as decreased ignition performance.

Patent document 2 discloses another way of holding a heat source, in which a sleeve is composed of an outer and an inner sleeves, the inner sleeve being folded back to hold the heat source by elasticity. The smoking article disclosed in patent document 2 is however complicated in structure. A variety of ways of holding the carbon heat source, including these, have been proposed. In any case, the carbon heat source needs to be reliably held so as not to come off the end of the smoking article during use.

PRIOR-ART DOCUMENT

Patent Document

Patent document 1: WO 2007/119678 A1
Patent document 2: JP 3012253 B2

SUMMARY OF THE INVENTION

Problem to be Solved by the Invention

The present invention has been made in view of the prior art described above. An object of the present invention is to provide a smoking article in which reliable holding of a carbon heat source can be created efficiently without use of a heat-insulating jacket formed from a glass mat or the like, and which is constructed from a reduced number of components with a reduced number of assembling steps, and thus, achieves a reduction in costs.

Means for Solving the Problem

In order to achieve the above object, the present invention provides a smoking article comprising a multilayered tube member including at least one metal layer and one paper layer, a carbon heat source arranged in an end portion of the tube member to be at least partly in direct close contact with an inner surface of the tube member, the carbon heat source emitting heat when ignited, a smoking flavor releasing source arranged in the tube member to adjoin the carbon heat source, and a holder part keeping the carbon heat source in direct contact with said end portion and holding the carbon heat source against said end portion.

Desirably, the holder part has a circumferential projection on an inner surface, the circumferential projection continuously extending circumferentially on the inner surface.

Desirably, the holder part has a plurality of projections on an inner surface.

Desirably, the holder part has a plurality of axial projections on an inner surface, the axial projections extending axially on the inner surface.

Desirably, the holder part is folded back inward to have a turned edge.

Desirably, the carbon heat source has a circumferential groove adapted to engage with said circumferential projection.

Desirably, the smoking article further comprises a through hole formed in the carbon heat source to intersect the axis of the carbon heat source, and a pin inserted into the holder part to extend through the through hole.

Desirably, the carbon heat source has a threaded circumferential surface.

Desirably, the carbon heat source has an outside diameter greater than an inside diameter of the holder part so that the carbon heat source is pressed into the holder part.

Desirably, the carbon heat source has a tapered surface tapering in the direction in which the carbon heat source is pressed into the holder part.

Desirably, the smoking article further comprises a filter connected to the tube member by tip paper.

Effect of the Invention

In the present invention, the carbon heat source is held in the holder part constituting an end portion of the tube member, in direct contact with the holder part. This allows the carbon heat source to have an increased diameter compared with the prior art, leading to increased ignition performance. To hold the carbon heat source, a (holding) member separate from the holder part, such as a heat-insulating jacket formed from a glass mat or the like, is not needed. This leads to a reduced number of components and a reduced number of assembly steps, and thus, increased working efficiency. This also leads to a reduction in costs.

The holder part with a circumferential projection can reliably hold the carbon heat source by pressing it.

The holder part with a plurality of projections, for example axial projections can reliably hold the carbon heat source.

The holder part may have a turned edge formed by folding the holder part back inward. Such holder part can reliably hold the carbon heat source by the turned edge pressing the carbon heat source.

The carbon heat source may have a circumferential groove. Engagement between the circumferential groove and the aforementioned circumferential projection provides increased reliability of holding.

The reliability of holding can also be increased by inserting a pin into the holder part to extend through a through hole in the carbon heat source.

The reliability of holding can also be increased by forming a thread on the carbon heat source.

The carbon heat source may be formed with an outside diameter greater than an inside diameter of the holder part so that the carbon heat source can be pressed into the holder part and reliably held therein. In this case, if the carbon heat source has a tapered surface, it can be pressed into the carbon heat source with ease, and thus, the holding of the carbon heat source can be created efficiently.

MODE OF CARRYING OUT THE INVENTION

Figure 1:
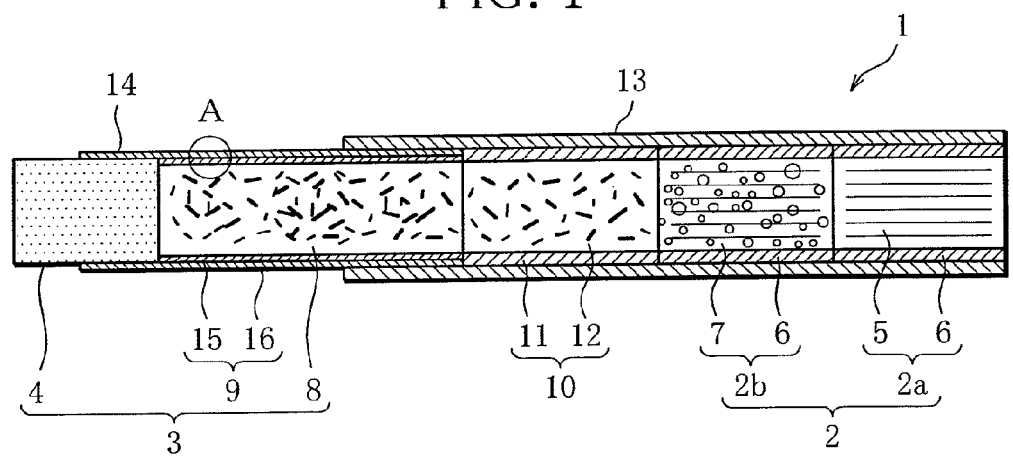
FIG. 1 is a schematic cross-sectional view of a smoking article according to the present invention.

As seen in FIG. 1, a smoking article 1 according to the present invention comprises a tobacco rod 3. The tobacco rod 3 comprises a carbon heat source 4, a smoking flavor releasing source 8 and a non-combustible wrapper (tube member) 9. The tobacco rod 3 is aligned with a filter 2. The filter 2 is located at a mouth end. In the illustrated example, the filter 2 is a double filter composed of a plain filter segment 2a and a charcoal filter segment 2b. The filter 2 is however not restricted to this type. The plain filter segment 2a is formed by wrapping filter fiber 5 in rolling paper 6. The charcoal filter segment 2a is formed by wrapping activated carbon-containing filter fiber 7 in rolling paper 6. Although omitted in the illustration, the filter 2 is further wrapped in forming paper. The tobacco rod 3 is formed by wrapping a tobacco shreds-containing smoking flavor releasing source 8 in a non-combustible wrapping material 9. Specifically, the non-combustible wrapping material 9 is formed into a hollow cylinder, in which glycerin-containing tobacco sheets and destemmed tobacco shreds, which form the smoking flavor releasing source 8, are packed. In the illustrated example, an intermediate rod 10 is arranged between the tobacco rod 3 and the filter 2. The intermediate rod 10 is formed by wrapping tobacco shreds 12 in rolling paper 11. Specifically, the rolling paper 11 is formed into a hollow cylinder, in which tobacco shreds 12, more specifically, flavorings and destemmed tobacco shreds are packed. The tobacco rod 3 is connected to the filter 2 and the intermediate rod 10 by tip paper 13.

Figure 2:
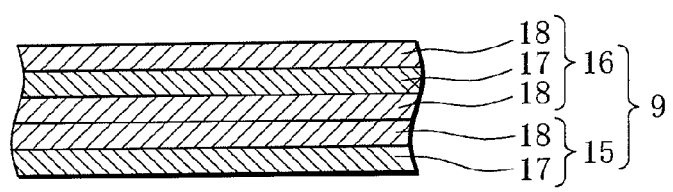
FIG. 2 is an enlarged view of part A of FIG. 1.

An end portion of the non-combustible wrapper 9 forms a holder part 14. Specifically, as seen in FIG. 2, the non-combustible wrapping material 9 is formed by bonding a three-layer composite sheet 16 to the outer side of a two-layer composite sheet 15. The part of the three-layer composite sheet 16 projecting from the two-layer composite sheet 15 forms the holder part 14. The two-layer composite sheet 15 comprises an inner layer of a metal, for example aluminum layer 17, and an outer layer of paper, or paper layer 18. The three-layer composite sheet 16 comprises a paper layer 18, an aluminum layer 17 and a paper layer 18 stacked in this order from the inside. The innermost layer of the non-combustible wrapper 9 is the aluminum layer 17. Thus, even when the temperature of the tobacco shreds increases during use, the aluminum layer 17 prevents heat transfer, and thus, the non-combustible wrapper 9 is not heated. Further, the aluminum layer 17 with good heat conductivity can efficiently heat the smoking flavor releasing source 8. The aluminum layer 17 may be replaced with a layer of any desired material having heat insulation capacity and heat conductivity.

The carbon heat source 4 is held in the holder part 14, in direct close contact with the holder part 14. The holder part 14 designed to directly contact and hold the carbon heat source does not require a holding member formed from a glass mat or the like to hold the carbon heat source 4. This leads to a reduced number of components and a reduced number of assembly steps, and thus, increased working efficiency. This also leads to a reduction in costs. The three-layer composite sheet 16 forming the holder part 14 also includes an aluminum layer 17, which prevents heat loss resulting from heat transfer from the carbon heat source 4 to the holder part 14.

Figure 3:
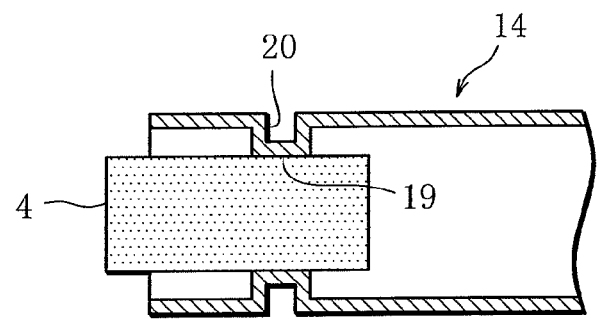
FIG. 3 is a schematic cross-sectional view of a part holding a carbon heat source of a smoking article according to the present invention.

Holding of the carbon heat source 4 by the holder part 14 may be achieved in the following manners:

In an example shown in FIG. 3, the holder part 14 has a circumferential projection 19. The circumferential projection 19 is provided on the inner surface of the holder part 14 to continuously extend circumferentially. The holder part 14 with the circumferential projection 19 can keep the carbon heat source 4 in close contact with the non-combustible wrapper 9 and directly engage with the carbon heat source 4, thereby reliably holding the carbon heat source. In the example shown in FIG. 3, in order to form the circumferential projection 19, a circumferential groove 20 is formed in the outer surface of the holder part. In other words, the circumferential projection 19 is formed by forming the circumferential groove 20. The holding of the carbon heat source 4 may be achieved by inserting the carbon heat source 4 in the holder part 14 and then pressing the holder part from outside to form the circumferential groove 20 and thus the circumferential projection 19, or alternatively, by forming the circumferential projection 19 in advance and then pressing the carbon heat source 4 into the holder part with the circumferential projection. Also in the examples shown in FIGS. 4 and 5 described next, these alternative ways are applicable to achieve the holding of the carbon heat source.

Figure 4:
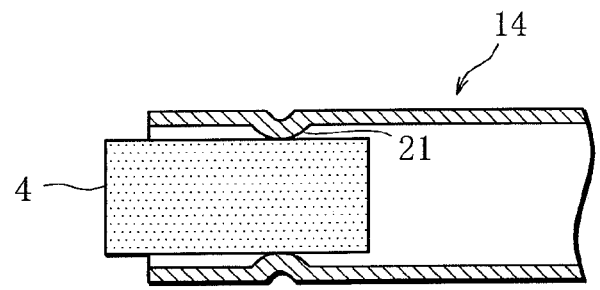
FIG. 4 is a schematic cross-sectional view of a part holding a carbon heat source of another smoking article according to the present invention.
Figure 5:
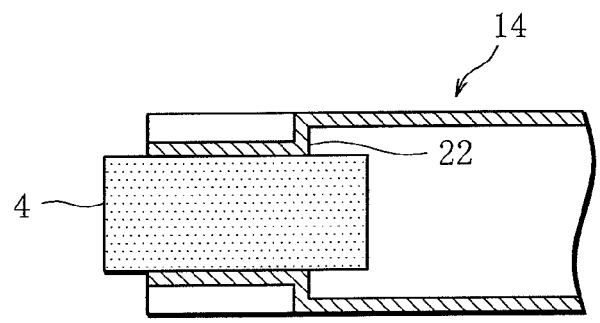
FIG. 5 is a schematic cross-sectional view of a part holding a carbon heat source of another smoking article according to the present invention.
Figure 6:
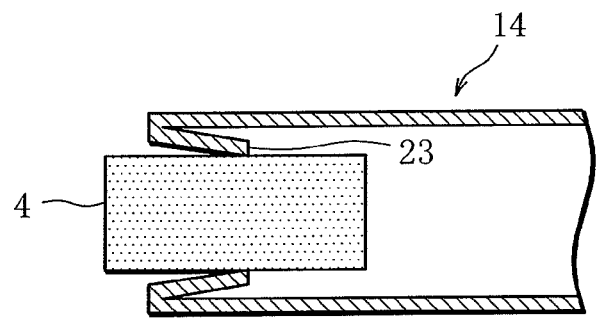
FIG. 6 is a schematic cross-sectional view of a part holding a carbon heat source of another smoking article according to the present invention.

In the example shown in FIG. 4, the holder part 14 has a plurality of projections 21 on the inner surface. The holder part 14 with the projections 21 can keep the carbon heat source 4 in close contact with the non-combustible wrapper 9 and directly engage with the carbon heat source 4, thereby reliably holding the carbon heat source. In the example shown in FIG. 5, the holder part 14 has a plurality of axial projections 22 on the inner surface. The axial projections 22 extend axially on the inner surface of the holder part 14. The holder part with such axial projections can more reliably hold the carbon heat source 4. As shown in FIG. 6, the holder part 14 may be folded back inward to have a turned edge 23. By the resilience of the turned edge 23, the holder part 14 can keep the carbon heat source 4 in close contact with the non-combustible wrapper 9 and directly engage with the carbon heat source 4, thereby reliably holding the carbon heat source.

Figure 7:
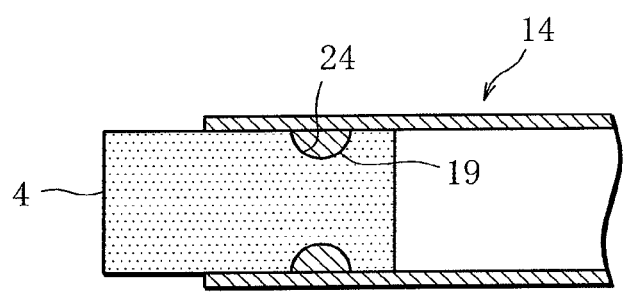
FIG. 7 is a schematic cross-sectional view of a part holding a carbon heat source of another smoking article according to the present invention.
Figure 8:
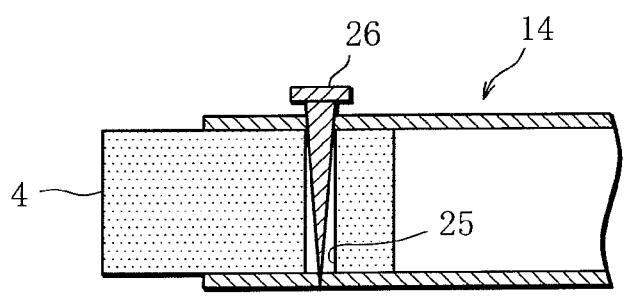
FIG. 8 is a schematic cross-sectional view of a part holding a carbon heat source of another smoking article according to the present invention.
Figure 9:
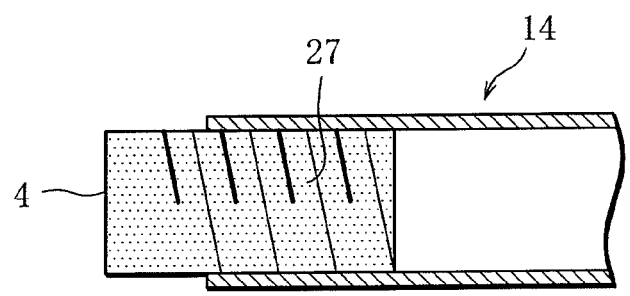
FIG. 9 is a schematic cross-sectional view of a part holding a carbon heat source of another smoking article according to the present invention.
Figure 10:
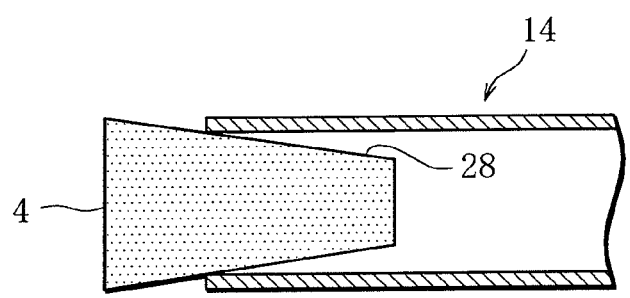
FIG. 10 is a schematic cross-sectional view of a part holding a carbon heat source of another smoking article according to the present invention.

As in the example shown in FIG. 7, a circumferential groove 24 may be formed in the carbon heat source 4 to engage with the aforementioned circumferential projection 19. The engagement between the circumferential projection 19 and the circumferential groove 24 produces reliable holding of the carbon heat source 4. In other words, the reliability of holding is increased by making an alternation to the carbon heat source 4 in addition to the holder part 14. FIG. 8 shows another example of making an alteration to the carbon heat source 4. As seen therein, a through hole 25 may be formed in the carbon heat source 4 for a pin 26 to extend through. Specifically, the pin 26 is inserted into the holder part 14 to extend through the through hole 25. As a result, engagement between the holder part 14 and the carbon heat source 4 is created indirectly by the pin 26, so that the carbon heat source 4 is held with increased reliability. As shown in FIG. 9, a thread 27 may be formed on the circumferential surface of the carbon heat source 4. Provision of the thread 27 also increases the reliability of holding.

To be pressed into the holder part 14, the carbon heat source 4 may be formed with an outside diameter greater than the inside diameter of the holder part 14. Desirably, as shown in 10, the carbon heat source 4 has a tapered surface 28 tapering in the direction in which the carbon heat source is pressed into the holder part 14. The carbon heat source 4 with such tapered surface can be pressed into the holder part with ease. In addition, the carbon heat source 4 with such tapered surface can be kept in close contact with the non-combustible wrapper 9 and directly engage with the holder part 14, and thus, be reliably held.

Experiment for comparing a non-combustible wrapper with a circumferential groove 20 as shown in FIG. 3 and a non-combustible wrapper without a circumferential groove was conducted. The non-combustible wrappers used measured 50 mm in length and 7.4 mm in inside diameter. The circumferential groove 20 was formed with a depth 0.2 mm so that the circumferential projection had an inside diameter 7.0 mm. The carbon heat sources used measured 7.1 mm to 7.3 mm in outside diameter and 10 mm in length. Smoking articles were formed by inserting a carbon heat source, as specified above, in each to-be-tested non-combustible wrapper by a length 5 mm, and attaching a filter. The smoking articles were sucked on under predetermined conditions, and then struck by a 200 gf force ten times to see whether the carbon heat source fell off. Twenty of smoking articles having a non-combustible wrapper with a circumferential groove and twenty of smoking articles having a non-combustible wrapper without a circumferential groove were examined. In all the twenty smoking articles having a non-combustible wrapper without a circumferential groove, the carbon heat source fell off, while in all the twenty smoking articles having a non-combustible wrapper with a circumferential groove, and thus, a circumferential projection, the carbon heat source remained held. Thus, the experiment confirmed that the smoking articles according to the present invention are effective in holding the carbon heat source. Incidentally, the test to see whether the carbon heat source fell off was conducted with a test apparatus capable of holding a smoking article at a fulcrum nearer to the filter-side end and swinging it up and down on the fulcrum many times, wherein the test apparatus was arranged such that the smoking article struck a receiving member with an end opposite to the filter end whenever swung down. Specifically, a test apparatus disclosed in JP 3048036 B2 was used.

EXPLANATION OF REFERENCE CHARACTERS

1 Smoking article
2 Filter
2a Plain filter
2b Charcoal filter
3 Tobacco rod
4 Carbon heat source
5 Filter fiber
6 Rolling paper
7 Activated carbon-containing filter fiber
8 Tobacco shreds
9 Non-combustible wrapper (tube member)
10 Intermediate rod
11 Rolling paper
12 Tobacco shreds
13 Tip paper
14 Holder part
15 Two-layer composite sheet
16 Three-layer composite sheet
17 Aluminum layer
18 Paper layer
19 Circumferential projection
20 Circumferential groove
21 Projection
22 Axial projection
23 Turned edge
24 Circumferential groove
25 Through hole
27 Thread
28 Tapered surface

The invention claimed is:

1. A smoking article comprising:
a tube member which is made of a non-combustible wrapper,
a carbon heat source arranged in an end portion of the tube member to be at least partly in direct close contact with an inner surface of the tube member, the carbon heat source emitting heat when ignited,
a smoking flavor releasing source arranged in the tube member to adjoin the carbon heat source, and
a holding device holding the carbon heat source against said end portion of the tube member, the holding device including a groove formed in an outer surface of the carbon heat source and a projection formed on the inner surface of the tube member,
wherein the groove has groove walls spaced out in an axial direction of the tube member, and the projection is fitted into the groove.

2. The smoking article according to claim 1, wherein the projection continuously extends around the circumferential of the tube member.

3. The smoking article according to claim 2, wherein the groove continuously extends circumferentially in the inner surface of the tube member to engage with said circumferential projection.

4. The smoking article according to claim 1, wherein the carbon heat source has a thread formed on the outer surface thereof, the thread providing the groove.

5. A smoking article according to claim 1, further comprising a filter connected to the tube member by tip paper.

6. The smoking article according to claim 1, wherein said non-combustible wrapper has a multilayer structure including at least one metal layer and one paper layer.

* * * * *